(12) United States Patent
McDermott et al.

(10) Patent No.: US 11,419,882 B2
(45) Date of Patent: Aug. 23, 2022

(54) VITAMIN D COMPOUNDS AND METHODS OF USING THE SAME

(71) Applicant: ALLERGYINTELLECT, INC, Glenwood Springs, CO (US)

(72) Inventors: Robert McDermott, Glenwood Springs, CO (US); Neal Jain, Glenwood Springs, CO (US)

(73) Assignee: ALLERGYINTELLECT, INC

( * ) Notice: Subject to any disclaimer, the term of this patent is extended or adjusted under 35 U.S.C. 154(b) by 27 days.

(21) Appl. No.: 16/620,376

(22) PCT Filed: Jun. 8, 2018

(86) PCT No.: PCT/US2018/036742
§ 371 (c)(1),
(2) Date: Dec. 6, 2019

(87) PCT Pub. No.: WO2018/227146
PCT Pub. Date: Dec. 13, 2018

(65) Prior Publication Data
US 2020/0179410 A1   Jun. 11, 2020

Related U.S. Application Data

(60) Provisional application No. 62/637,882, filed on Mar. 2, 2018, provisional application No. 62/517,069, filed on Jun. 8, 2017.

(51) Int. Cl.
| | | |
|---|---|---|
| A61K 31/593 | (2006.01) | |
| A61K 35/742 | (2015.01) | |
| A61K 35/747 | (2015.01) | |
| A61P 37/08 | (2006.01) | |
| A61P 17/04 | (2006.01) | |

(52) U.S. Cl.
CPC .......... *A61K 31/593* (2013.01); *A61K 35/742* (2013.01); *A61K 35/747* (2013.01); *A61P 17/04* (2018.01); *A61P 37/08* (2018.01)

(58) Field of Classification Search
None
See application file for complete search history.

(56) References Cited

U.S. PATENT DOCUMENTS

| | | | |
|---|---|---|---|
| 7,025,998 B2 | 4/2006 | Senin et al. | |
| 10,780,072 B2* | 9/2020 | Hazen | A61K 31/145 |
| 2009/0060878 A1 | 3/2009 | Clymer et al. | |
| 2013/0089572 A1 | 4/2013 | Vanderhoof et al. | |
| 2013/0344042 A1* | 12/2013 | Tanbonliong | A23L 33/18 424/93.45 |
| 2019/0261669 A1* | 8/2019 | Tripp | A23C 9/1307 |
| 2020/0179410 A1* | 6/2020 | McDermott | A61P 11/00 |

FOREIGN PATENT DOCUMENTS

| | | | | |
|---|---|---|---|---|
| CA | 3066620 A1 * | 12/2018 | | A61K 35/747 |
| DE | 10206995 | 9/2003 | | |
| WO | WO-2018227146 A1 * | 12/2018 | | A61P 17/00 |

OTHER PUBLICATIONS

Gerasimov et al., Nutrients, 2018, 10, 1975, 15 pages. (Year: 2018).*
Liao et al, Scientific Reports. 6:20481;doi:10.1038/srep20481(2016). published: Feb. 9, 2016. (Year: 2016).*
International Search Report and Written Opinion dated Sep. 10, 2018 in Application No. PCT/US18/36742.
International Preliminary Report on Patentability dated Dec. 10, 2019 in Application No. PCT/US18/36742.
Yu et al., "Vitamin D3 inhibits micro RNA-17-92 to promote specific immunotherapy in allergic rhinitis", Scientific Reports, Published Online: Apr. 3, 2017, vol. 7, Article No. 546. pp. 1-8; Downloaded from: https:/tlwww.nature.com/articles/s41598-017-00431-1.
Shi et al., "Specific immunotherapy in combination with Clostridium butyricum inhibits allergic inflammation in the mouse intestine," 2015, vol. 5, article 17651, pp. 1-9; DOI: 10.1038/srep17651. abstract; p. 2, Fig 1.

* cited by examiner

*Primary Examiner* — Nita M. Minnifield
(74) *Attorney, Agent, or Firm* — Procopio, Cory, Hargreaves & Savitch, LLP

(57) ABSTRACT

The present disclosure provides a composition comprising a first amount of a Vitamin D compound and a second amount of a probiotic compound. The disclosure also provides a method of treating an atopic condition in a subject in need thereof comprising administering to the subject a therapeutically effective amount of the composition detailed herein.

4 Claims, No Drawings

VITAMIN D COMPOUNDS AND METHODS OF USING THE SAME

CROSS REFERENCE TO RELATED APPLICATIONS

This application is a U.S. national stage entry under 35 U.S.C. § 371 of International Application No. PCT/US2018/036742 filed Jun. 8, 2018 entitled "VITAMIN D COMPOUNDS AND METHODS OF USING THE SAME," which claims priority to, and the benefit of, U.S. Provisional Patent Application No. 62/517,069 filed on Jun. 8, 2017, entitled "VITAMIN D COMPOUNDS AND METHODS OF USING THE SAME," and U.S. Provisional Patent Application No. 62/637,882, filed on Mar. 2, 2018, entitled "VITAMIN D COMPOUNDS AND METHODS OF USING THE SAME." Each of the foregoing applications are hereby incorporated by reference in their entirety.

FIELD

The present disclosure relates to Vitamin-based compositions. In particular, the disclosure relates to compositions that comprise Vitamin D3 compounds.

BACKGROUND

Allergic diseases such as allergic rhinitis, asthma, atopic dermatitis, and food allergy are becoming increasingly prevalent. It is estimated that 40 million Americans suffer from allergic asthma, 60 million suffer from allergic rhinitis, 10 million suffer from food allergy, and another 35 million suffer from atopic dermatitis.

The proposed reasons behind the rise in allergic disease include suggestions that alteration in our normal gut, skin, and respiratory microbiome may affect our normal epithelial barrier function and immune response to antigen.

Although many medical therapies exist to help manage atopic conditions, including corticosteroid therapies, few natural supplements have been proposed to help balance the altered immune response that occurs in these conditions.

According to the latest National Health Interview Survey, the use of probiotics in the United States was four times higher, up to 3.9 million, in 2012 than in 2007. This makes probiotics the 3$^{rd}$ most used natural supplement in the United States. Additionally, Vitamin D3 deficiency is estimated to be between 40-45% in the United States. It is felt to be the most widely recommended vitamin supplement recommended by doctors as deficiency is common, with relatively low risk when used at low doses (1000-2000 IU).

The organisms that comprise the gut microbiome are complex and diverse and a variety of factors including diet and environment (rural vs. urban) can influence the composition of the gut microbiome. Growing evidence suggests that the composition of the gut microbiome may dramatically influence immune responses to antigen.

Data suggests that certain bacteria, specifically those from the class Clostridia, promote development of tolerance in the gut. Clostridia can promote tolerance in the gut through several mechanisms including promotion of a TGF-β/IL-10, Foxp3$^+$ T-regulatory rich environment and through IL-18 and IL-22 production which promotes epithelial integrity and up-regulates expression of mucous and antimicrobial peptides.

The mechanism by which Clostridia promotes gut tolerance and anti-allergy effects is not entirely known however data suggests that the products of bacterial metabolism likely play a large role in the positive immune responses. The clostridia families Lachnospiraceae and Ruminococcaceae are among prominent bacterial groups in the proximal colon that ferment dietary fiber to produce short-chain fatty acids (SCFAs) including most notably butyric acid, which seems to have multiple protective, tolerance inducing effects on the immune response. Consistent with the observations that the microbiome can promote gut tolerance to allergen, perturbations of the microbiome correlate with development of allergic disease including food allergy. Early antibiotic exposure in life can adversely affect the microbiome later in life and such exposure increases the risk for development of food allergy, and persistence of food allergy later in life (Chinthrajah et al., J Allergy Clin Immunol 2016; 137:984-97).

Vitamin D3 has been shown to have an important role in adaptive and innate immune responses and may be important in the function of regulatory t-cells. Vitamin D has been demonstrated to be important in regulation normal immune function and host response against upper respiratory infections (Ginde et al., Arch Inter Med 2009; 169:384-90). Additionally, Vitamin D therapy may be effective in patients with atopic dermatitis, as it has been shown in vivo that Vitamin D stimulates cathelicidin production where reduced levels of cathelicidin is associated with increased colonization of staphylococcal bacteria (Antal et al., Dermatoendocrinol. 2011; 3(1):18-22). Vitamin D also appears to have a role in chronic idiopathic urticaria and food allergy and anaphylaxis.

SUMMARY

In an aspect, a composition is disclosed, comprising a first amount of a Vitamin D compound and a second amount of a probiotic compound. In embodiments, the Vitamin D compound comprises a Vitamin D3 compound. In embodiments, the first amount of the Vitamin D comprises about 1000 IU, about 2000 IU, about 4000 IU, or about 5000 IU of the Vitamin D compound. In embodiments, the second amount of the probiotic compound comprises about 3M CFU, about 10 M CFU, about 1B CFU, or about 10B CFU of the probiotic compound. In embodiments, the probiotic compound comprises any one or more of *Bifidobacterium animalis, Bacteroides uniformis, Clostridium butyricum, Lactobacillus rhamnosus, Enterococcus faecalis,* or *Bacillus mesentericus*. In embodiments, the probiotic compound comprises *Clostridium butyricum*. In embodiments, the probiotic compound comprises *Lactobacillus rhamnosus*.

In another aspect, a method of treating an atopic condition in a subject in need thereof is disclosed. The method comprises administering to the subject a therapeutically effective amount of the composition as described herein. In embodiments, the atopic condition is selected from allergic rhinitis, atopic dermatitis, eosinophilic esophagitis, chronic idiopathic urticaria, food allergy, or asthma.

In another aspect, a method of treating a non-atopic condition in a subject in need thereof is disclosed. The method comprises administering to the subject a therapeutically effective amount of the composition as described herein. In embodiments, the non-atopic condition may be selected from inflammatory bowel disease, irritable bowel syndrome with constipation, irritable bowel syndrome with diarrhea, chronic urticaria, non-allergic chronic rhinitis, psoriasis, rheumatoid arthritis, or food intolerance.

DETAILED DESCRIPTION

Definitions and Interpretation

The detailed description shows exemplary embodiments. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step.

In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where and if a phrase similar to "at least one of A, B, and C" or "at least one of A, B, or C" is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The term "atopic condition" as used herein means any condition involving an allergy or an allergic reaction.

The term "CFU" as used herein means a colony-forming unit.

The term "IU" as used herein means an international unit of the substance to for which it is being used.

The term "non-atopic condition" as used herein means any condition not involving an allergy or an allergic reaction.

The term "probiotic compound" as used herein means any compound containing micro-organisms that confers a health benefit when administered to a host.

The term "therapeutically effective amount" refers to a sufficient quantity of the active agents of the present invention, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

The term "Vitamin D compound" as used herein means any compound containing Vitamin D.

The term "Vitamin D3 compound" as used herein means any compound containing Vitamin D3.

Words that are not specifically defined herein will be understood to have a meaning consistent with that as understood by persons of ordinary skill in the art.

Description of Aspects of the Disclosure

In an aspect, a composition is disclosed comprising a first amount of a Vitamin D compound and a second amount of a probiotic compound. The composition may further comprise a prebiotic for packaging purposes and for stability of the active ingredients. The prebiotic may comprise *psyllium* or cellulose. The first amount of the Vitamin D compound may be in a tablet or capsule form. The first amount of the Vitamin D compound and the second amount of the probiotic compound may be mixed together to form a homogenous mixture.

In embodiments, the Vitamin D compound comprises a Vitamin D3 compound. In embodiments, the first amount comprises between about 1000 IU and about 4000 IU of the Vitamin D compound. In embodiments, the first amount comprises about 1000 IU, about 2000 IU, about 4000 IU, or about 5000 IU of the Vitamin D compound. In embodiments, the first amount comprises about 1000 IU, about 1100 IU, about 1200 IU, about 1300 IU, about 1400 IU, about 1500 IU, about 1600 IU, about 1700 IU, about 1800 IU, about 1900 IU, 2000 IU, about 2100 IU, about 2200 IU, about 2300 IU, about 2400 IU, about 2500 IU, about 2600 IU, about 2700 IU, about 2800 IU, about 2900 IU, 3000 IU, about 3100 IU, about 3200 IU, about 3300 IU, about 3400 IU, about 3500 IU, about 3600 IU, about 3700 IU, about 3800 IU, about 3900 IU, or about 4000 IU about 4100 IU, about 4200 IU, about 4300 IU, about 4400 IU, about 4500

IU, about 4600 IU, about 4700 IU, about 4800 IU, about 4900 IU, or about 5000 IU of the Vitamin D compound.

In embodiments, the composition comprises a second amount of a probiotic compound. In embodiments, the probiotic compound comprises any one or more of *B. animalis, B. uniformis, C. butyricum, L. rhamnosus, E. faecalis,* or *B. mesentericus.* In embodiments, the second amount comprises between about 0.5M CFU and about 10B CFU of the probiotic compound. In embodiments, the second amount comprises about 3M CFU, about 10 M CFU, about 1B CFU, or about 10B CFU of the probiotic compound. In embodiments, the second amount comprises about 0.5M CFU, about 0.6M CFU, about 0.7M CFU, about 0.8M CFU, about 0.9M CFU, about 1M CFU, about 1.1M CFU, about 1.2M CFU, about 1.3M CFU, about 1.4M CFU, about 1.5M CFU, about 2.0M CFU, about 2.5M CFU, about 3M CFU, about 4M CFU, about 5M CFU, about 6M CFU, about 7M CFU, about 8M CFU, about 9M CFU, about 10M CFU, about 50M CFU, about 100 M CFU, about 150 M CFU, about 200 M CFU, about 250 M CFU, about 300 M CFU, about 350 M CFU, about 400 M CFU, about 450 M CFU, about 500 M CFU, about 550 M CFU, about 600 M CFU, about 650 M CFU, about 700 M CFU, about 750 M CFU, about 80 M CFU, about 850 M CFU, about 900 M CFU, about 950 M CFU, about 1B CFU, about 2B CFU, about 3B CFU, about 4B CFU, about 5B CFU, about 6B CFU, about 7B CFU, about 8B CFU, about 9B CFU, or about 10B CFU of the probiotic compound.

In embodiments, the probiotic compound may comprise any one or more of *Lactobacillus acidophilus* (CUL 60), *Lactobacillus acidophilus* (CUL 21). *Bifidobacterium bifidum* (CUL 20), *Bifidobacterium lactis* (CUL 34), *Lactococcus lactis, Lactobacillus gasseri, Bifidobacterium animals* subsp. *Lactis* (A026), *Bifidobacterium breve* (A055), *Enterococcus faecium* T-110, *Bacillus subtilis* TO-A, *Bifidobacterium, Bacillus coagulans, Lactobacillus plantarum,* or *Streptococcus* Hermophilus. In embodiments, the second amount comprises between about 0.5M CFU and about 10B CFU of the probiotic compound. In embodiments, the second amount comprises about 3M CFU, about 10 M CFU, about 1B CFU, or about 10B CFU of the probiotic compound. In embodiments, the second amount comprises about 0.5M CFU, about 0.6M CFU, about 0.7M CFU, about 0.8M CFU, about 0.9M CFU, about 1M CFU, about 1.1M CFU, about 1.2M CFU, about 1.3M CFU, about 1.4M CFU, about 1.5M CFU, about 2.0M CFU, about 2.5M CFU, about 3M CFU, about 4M CFU, about 5M CFU, about 6M CFU, about 7M CFU, about 8M CFU, about 9M CFU, about 10M CFU, about 50M CFU, about 100 M CFU, about 150 M CFU, about 200 M CFU, about 250 M CFU, about 300 M CFU, about 350 M CFU, about 400 M CFU, about 450 M CFU, about 500 M CFU, about 550 M CFU, about 600 M CFU, about 650 M CFU, about 700 M CFU, about 750 M CFU, about 80 M CFU, about 850 M CFU, about 900 M CFU, about 950 M CFU, about 1B CFU, about 2B CFU, about 3B CFU, about 4B CFU, about 5B CFU, about 6B CFU, about 7B CFU, about 8B CFU, about 9B CFU, or about 10B CFU of the probiotic compound.

In another aspect, a method of treating an atopic condition in a subject in need thereof is disclosed. The method comprises administering to the subject a therapeutically effective amount of the composition described herein. In embodiments, the condition may comprise an atopic condition. In embodiments, the atopic condition may be selected from allergic rhinitis, atopic dermatitis, eosinophilic esophagitis, chronic idiopathic urticaria, food allergy, or asthma.

In another aspect, a method of treating a non-atopic condition in a subject in need thereof is disclosed. The method comprises administering to the subject a therapeutically effective amount of the composition as described herein. In embodiments, the non-atopic condition is selected from inflammatory bowel disease, irritable bowel syndrome with constipation, irritable bowel syndrome with diarrhea, chronic urticaria, non-allergic chronic rhinitis, psoriasis, rheumatoid arthritis, or food intolerance.

Atopic Diseases

Aspects of this disclosure focus on atopic diseases. Atopic diseases pose a great burden to the individual and society. The word atopy refers to an inherited tendency to produce immunoglobulin E (IgE) antibodies in response to small amounts of common environmental proteins such as pollen, house dust mite, and food allergens. The presence of atopy in an individual is associated with an increased risk of developing one or more of the atopic diseases, including allergic rhinitis, also known as hay fever, atopic dermatitis, eosinophilic esophagitis, chronic idiopathic urticaria, food allergy, and asthma. In childhood the incidence of atopic manifestations may be higher among boys, but this tendency changes in adolescence and in adulthood, during which girls may become more symptomatic. Although the skin sensitization occurring in atopic dermatitis appears to be the trigger for the subsequent development of the other allergic conditions, the progression is not uniform in all atopic children. Allergic manifestations can develop at any point in life.

Many risk factors for atopic diseases have been identified. Having a close relative with an atopic disease may be one of the most distinct risk factors for one's own development of an atopic disease. Sensitization to aeroallergens such as house dust mite, animal dander, or pollen may be a strong risk factor for development of atopic diseases, particularly asthma and hay fever.

Atopic dermatitis is primarily a disease of early childhood. About 20% of all children develop symptoms of atopic dermatitis at some point in their lives. Half of these develop symptoms within the first year of life with 95% experiencing onset below 5 years of age. The risk of other atopic diseases, primarily asthma and hay fever, is markedly increased in children with atopic dermatitis. A child with moderate to severe atopic dermatitis has a 50% risk of developing asthma, either concomitantly or in later life, whereas the risk of developing hay fever is as much as 75%.

Regarding food allergies, more than 170 foods have been reported to cause IgE-mediated reactions, but the allergens most commonly involved are cow's milk, egg, nuts, fish, and shellfish. Food allergy is associated with the occurrence of other atopic disorders. About 50% of all children with food allergy have atopic dermatitis, about 40% have asthma, and about 30% have allergic rhinitis.

Regarding asthma, a diagnosis in children under 3 years of age may be difficult since many young children have recurrent episodes of wheezing and cough, typically in response to acute respiratory infections. Moreover, measurement of lung function, airway inflammation and hyperresponsiveness is difficult in this age group. A positive family history of atopic disease, presence of atopic dermatitis and sensitization to food and aeroallergens may predict persistent asthma in childhood and in later life. The other atopic diseases may accompany or precede asthma, and about 40% of all children with asthma may have a history atopic dermatitis. Patients with atopic asthma have or may develop hay fever in more than 80% of the cases, whereas only 30% of patients with non-atopic asthma may have hay fever.

Allergic rhinitis/hay fever is present in about 20% of individuals from Western populations. It may develop in late childhood but is most frequent in subjects aged 20-40 years, after which the incidence gradually declines. In many with hay fever, symptoms may diminish in middle and late adulthood. Symptoms may occur in response to grass and tree pollen but also in relation to indoor allergens such as house dust mite and furred pets. Although most people experience seasonal symptoms, about 25% of all affected individuals have perennial symptoms. Seasonality is closely linked to allergic sensitization, often to outdoor allergens, with perennial symptoms being more common in subjects with non-atopic rhinitis. Non-atopic rhinitis is associated with nasal polyps, sinusitis, and recurrent headache.

Eosinophilic esophagitis is a chronic immune system disease in which a type of white blood cell (eosinophil) builds up in the lining of the esophagus. This buildup, which is a reaction to foods, allergens or acid reflux, can inflame or injure the esophageal tissue. Damaged esophageal tissue may lead to difficulty swallowing or cause food to get stuck when you swallow.

Chronic idiopathic urticaria (CIU) is a condition characterized by itch and hives that are idiopathic and last for 6 weeks or more. Women are twice as likely as men to experience CIU, and the greatest incidence is seen between 20 and 40 years of age. Hives may appear suddenly and may be recurrent. Generally, individual hives last less than 24 hours, but new hives may develop simultaneously at different sites on the skin.

Non-Atopic Diseases

The compositions detailed herein can also be used to treat non-atopic disease. Non-atopic diseases include inflammatory bowel disease, irritable bowel syndrome with constipation, irritable bowel syndrome with diarrhea, chronic urticaria, non-allergic chronic rhinitis, psoriasis, rheumatoid arthritis, and food intolerance.

Inflammatory bowel disease (IBD) is an umbrella term used to describe disorders that involve chronic inflammation of your digestive tract. Types of IBD include ulcerative colitis and Crohn's disease. Ulcerative colitis causes long-lasting inflammation and sores or ulcers in the innermost lining of your large intestine and rectum. Crohn's disease is characterized by inflammation of the lining of your digestive tract, which often spreads deep into affected tissues. Both ulcerative colitis and Crohn's disease usually involve severe diarrhea, abdominal pain, fatigue and weight loss. Signs and symptoms that are common to both Crohn's disease and ulcerative colitis include diarrhea, fever and fatigue, abdominal pain and cramping, blood in your stool, reduced appetite, and unintended weight loss.

Irritable bowel syndrome (IBS) is a common disorder that affects the large intestine. Signs and symptoms include cramping, abdominal pain, bloating, gas, and diarrhea or constipation, or both. IBS is a chronic condition that you'll need to manage long term.

Chronic urticaria is a condition characterized by hives that are red, itchy welts that result from a skin reaction. The welts vary in size and appear and fade repeatedly as the reaction runs its course. The condition is considered chronic hives if the welts appear for more than six weeks and recur frequently over months or years. Chronic urticaria can be very uncomfortable and interfere with sleep and daily activities.

Non-allergic chronic rhinitis involves chronic sneezing or a congested, drippy nose with no apparent cause. The symptoms of nonallergic chronic rhinitis are similar to those of hay fever (allergic rhinitis), but none of the usual evidence of an allergic reaction is present. Non-allergic chronic rhinitis can affect children and adults, but is more common after age 20. Triggers of non-allergic chronic rhinitis symptoms vary and can include certain odors or irritants in the air, changes in the weather, some medications, certain foods, and chronic health conditions.

Psoriasis is a common skin condition that speeds up the life cycle of skin cells. It causes cells to build up rapidly on the surface of the skin. The extra skin cells form scales and red patches that are itchy and sometimes painful. Psoriasis is a chronic disease.

Rheumatoid arthritis is a chronic inflammatory disorder that can damage a wide variety of body systems, including the skin, eyes, lungs, heart and blood vessels. An autoimmune disorder, rheumatoid arthritis occurs when your immune system mistakenly attacks your own body's tissues.

Food intolerance occurs when a person has difficulty digesting a particular food. This can lead to symptoms such as intestinal gas, abdominal pain or diarrhea. A food intolerance response takes place in the digestive system. It occurs when you are unable to properly breakdown the food.

Doses and Dosage Forms

In embodiments, the disclosed compositions may be administered to subject in need thereof in varying doses as detailed herein. The disclosed compositions may be administered periodically, such as once or twice a day, or any other suitable time period. For example, the disclosed compositions may be administered to a subject in need three times per week, twice, a week, once a week, once every other week, once every three weeks, once a month, every other month, every three months, every six months, every nine months, or once a year.

In embodiments, the disclosed compositions can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The disclosed compositions can also be formulated for injection, insufflation, infusion, or intradermal exposure. For instance, an injectable formulation may comprise the disclosed compositions in an aqueous or non-aqueous solution at a suitable pH and tonicity.

The disclosed compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the compositions may be a controlled release formulation, sustained release formulation, immediate release formulation, or any combination thereof. Further, the compositions may be a transdermal delivery system.

In embodiments, the compositions comprising can be formulated in a solid dosage form for oral administration, and the solid dosage form can be powders, granules, capsules, tablets or pills. In embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In embodiments, the disclosed compositions can be formulated as a nasal dosage form. Such dosage forms of the present invention comprise solution, suspension, and gel compositions for nasal delivery.

In embodiments, the disclosed compositions can be formulated in a liquid dosage form for oral administration, such as suspensions, emulsions or syrups. In embodiments, the liquid dosage form can include, in addition to commonly used simple diluents such as water and liquid paraffin, various excipients such as humectants, sweeteners, aromatics or preservatives. In embodiments, the disclosed compositions can be formulated to be suitable for administration to a pediatric patient.

In embodiments, the disclosed compositions can be formulated in a dosage form for parenteral administration, such as sterile aqueous solutions, suspensions, emulsions, non-aqueous solutions or suppositories. In some embodiments, the solutions or suspensions can include propyleneglycol, polyethyleneglycol, vegetable oils such as olive oil or injectable esters such as ethyl oleate.

The dosage of the disclosed compositions can vary depending on the patient's weight, age, gender, administration time and mode, excretion rate, and the severity of disease.

The following examples are given to illustrate the present invention. It should be understood, however, that the invention is not to be limited to the specific conditions or details described in these examples.

EXAMPLES

Example 1: Experimental Protocol

Experiments were designed to evaluate the efficacy and tolerability of a composition comprising varying quantities of Vitamin D3 (1000 IU, 2000 IU, and 4000 IU) taken together with varying quantities of *C. butyricum* and/or *L. rhamnosus*, and/or the short chain fatty acid sodium butyrate (600 mg). Excipients and prebiotics, such as cellulose or other fructo-oligosaccharides to help probiotic survival, for example, may be used for packaging purposes and for stability of the active ingredients. The experiments may require administration of two or more of the ingredients as separate capsules or tablets based on the ability to manufacture versus the need to outsource the individual ingredients.

Subjects undergoing specific subcutaneous or sublingual immunotherapy for allergic rhinitis with or without concomitant asthma were monitored for rhinitis symptoms over 12 weeks of supplementation.

Subjects with seasonal or perennial allergic rhinitis treatment versus placebo were monitored over 4 weeks of supplementation.

Females of childbearing age planning pregnancy or presently pregnant with a high risk of delivering an atopic infant were monitored over up to 12 weeks of supplementation. Infants were followed post-partum and monitored for the development of atopic dermatitis and/or food allergy for the first 6 months of life.

Breastfeeding mothers of infants who suffer from atopic dermatitis; infants SCORAD were monitored for 4 weeks of supplementation.

Subjects with a diagnosis of eosinophilic esophagitis who remained symptomatic despite food avoidance measures and/or swallowed steroid therapy were monitored over up to 12 weeks of supplementation.

Children, adolescents, and adults over the age of 8 years who suffer from atopic dermatitis were monitored via SCORAD for 4 weeks of supplementation.

Adults suffering with chronic urticaria were monitored for 8 weeks of supplementation.

Subjects A and B were administered either: 2000 IU Vitamin D3+3M CFU *C. butyricum;* 4000 IU Vitamin D3+10M CFU *C. butyricum;* 2000 IU Vitamin D3+1B CFU *L. rhamnosus;* 4000 IU Vitamin D3+10B CFU *L. rhamnosus;* 2000 IU Vitamin D3+300 mg sodium butyrate; 4000 IU Vitamin D3+600 mg sodium butyrate; 2000 IU Vitamin D3+3M CFU *C. butyricum*+1B CFU *L. rhamnosus*; or 4000 IU Vitamin D3+3M CFU *C. butyricum*+1B CFU *L. rhamnosus.*

Outcome measures for allergic rhinitis were measured by the "Rhinitis Control Assessment Test" (RCAT), a validated self-administered instrument for evaluating symptom control with patients with allergic rhinitis (Schatz et al., Ann Allergy Asthma Immunolo. 2010; 104:118-124).

Outcome measures for atopic dermatitis were measured by the "scoring atopic dermatitis" system (SCORAD), a validated clinical tool used to assess the extent and severity of eczema (Atherton et al., Dermatology 1993; 186:23-31).

Outcome measures for eosinophilic esophagitis were measured by the "Pediatric Eosinophilic Esophagitis Symptoms Scores" (PESS v2.0), a validated clinical tool to measure patient relevant outcomes for eosinophilic esophagitis (Martin et al., J Allergy Clin Immunol. 2015 June: 135(6): 1519-1528.e8).

Outcome measures for chronic idiopathic urticaria were monitored by the "Chronic Urticaria Quality of Life Questionnaire" (CU-Q2oL), a validated tool to assess quality of life in patients with chronic idiopathic urticaria (Zuberbier et al., Allergy 2009 October; 64(10):1417-26).

Example 2: Efficacy of Vitamin D/*C. butyricum* Composition

Subject A was enrolled in a study to investigate the efficacy of vitamin D in combination with *C. butyricum*. Vitamin D3 2000 IU was sourced from Costco (Kirkland brand 2000 unit gelcaps) and *C. butyricum* was sourced from Japan (Miyarisan tablets).

Subject A was a 45-year-old female with moderately severe spring and fall allergies. Partial symptom control in the past was obtained by using nasal steroids in combination with montelukast. In September of 2017, Subject A was experiencing moderately severe environmental allergy symptoms. Prior to initiating *C. butyricum* with Vitamin D, Subject A was not being treated with montelukast or nasal steroid. Environmental skin testing completed in September confirmed environmental allergen sensitivity to trees, grass, and weeds. After informed consent was obtained, Subject A was enrolled into the clinical trial. Total nasal symptom scores were monitored throughout the duration of treatment.

Subject A received 2000 IU of Vitamin D3 plus one capsule of *C. butyricum* twice per day throughout the duration of the investigation. Prior to the onset of the study, her total nasal symptom score for symptoms within the last 12 hours was 15 and symptoms over the previous two weeks was 5. During week one of the treatment, total nasal symptom scores for the 12-hour category were in the average of 6 and total nasal symptom score during week one was also 6. After three weeks of treatment, a total nasal symptom score for the 12-hour category was reduced to 0.73 and the total nasal symptom score for the two-week evaluation reduced to 4.2. These results indicate a significant reduction in total nasal symptom scores when the supplements of Vitamin D and *C. butyricum* were provided during a fall allergy season.

Subject B was enrolled in a study to investigate the efficacy of Vitamin D in combination with *C. butyricum*. Vitamin D3 2000 IU was sourced from Costco (Kirkland brand 2000 unit gelcaps) and *C. butyricum* was sourced from Japan (Miyarisan tablets).

Subject B was a 44 year-old male with a history of perennial allergic rhinitis and moderate to severe chronic sinusitis was enrolled. Subject B demonstrated sensitivity to a variety of pollens as well as to animal dander, dust mites, and molds. Subject B reported ongoing symptoms of sinus pressure, fatigue, and a frequent requirement for antibiotics and oral steroids. Subject B reported regularly performing nasal irrigations as well as using a nasal steroid spray (fluticasone) twice daily. Informed consent was obtained and Subject B was enrolled into the trial. Total nasal symptom scores (TNSS) were monitored during one week of run-in/placebo and during 4 weeks of treatment. Subject B reported experiencing a viral upper respiratory infection during week 4 of treatment with Vitamin D3 and *C. butyricum*.

During the run-in week Subject B's 12-hour TNSS was 9.7 and 2-week TNSS was 8.14. Subject B then began to ingest Vitamin D3 2000 IU twice daily and *C. butyricum* tablets twice daily. Subject B's 12-hour TNSS during the 4 week treatment decreased to 6.14 (a 36% reduction), and 2-week TNSS decreased to 3.07 (a 62% reduction).

Subject B tolerated the treatment well and seemed to indicate feeling as though the supplements were beneficial, without any adverse side effects. These results seem to indicate a positive response to the ingestion of *C. butyricum* and Vitamin D3 as a supplement to support immune and allergy health.

Example 3: Efficacy of Composition Comprising Vitamin D and a Probiotic

Subjects with a variety of atopic conditions including but not limited to allergic rhinitis, asthma, atopic dermatitis, food allergy, chronic urticaria, eosinophilic esophagitis, irritable bowel syndrome, a propensity towards recurrent infections and gastresophageal reflux disease were asked to consider taking a probiotic and Vitamin D3 as supplements between January 2018 and June 2018. Although not supplied to the subjects, it was recommended to take between 1000-4000 IU of Vitamin D3 and a probiotic compound containing either *Lactobacillus rhamnosus* and/or *Clostridium butyricum*.

Clinical Scoring System

Subjects were interviewed by phone about their perception of benefit or side effects associated with the use of the supplements they choose. Subjects were asked to rate on a 4 point scale, wherein a score of 1 was given if symptoms worsened; a score of 2 was given if there was no change in symptoms; a score of 3 was given if there was some improvement in symptoms; and a score of 4 was given if there were marked improvement in symptoms. Subjects were also asked for any additional information relating to the use of the probiotics and Vitamin D3.

Experimental Results

A subset of the results follows below:

Subject C was a 42 year-old Caucasian female with allergic rhinitis who had been on subcutaneous allergen immunotherapy for 3 years. She reported having supplementing daily with one capsule of the probiotic "HLC high potency capsules" without Vitamin D3 for many years. "HLC high potency capsules" were reported to comprise *L. acidophilus* (CUL 60), *L. acidophilus* (CUL 21), *B. bifidum* (CUL 20), *B. lactis* (CUL 34), with a reported cell count of 8 billion viable cells. She reports no perceived benefit with regards to the probiotic on improvement of symptoms of allergic rhinitis or efficacy of her allergen immunotherapy. A score of 2 was reported.

Subject D was a 64 year-old Caucasian female with eosinophilic esophagitis and GERD and reported taking Vitamin D3 4000 IU for 9 months without a probiotic compound. She does not perceive any benefit from the supplementation of Vitamin D3. A score of 2 was reported.

Subject E was a 38 year-old Caucasian female with allergic rhinitis and gastroesophageal reflux disease (GERD) who had been on subcutaneous allergen immunotherapy for less than one year. She reported supplementing daily for 10 months with Vitamin D3 2000 IU and 1 capsule of "Probiotic 5 Billion Cell Cap." It was reported that "Probiotic 5 Billion Cell Cap" comprises *L. lactis* 3.5B CFU, *L. gasseri* 0.5B CFU, *L. rhamnosus* 0.5B CFU, *B. animals* subsp. *Lactis* (A026) 0.4B CFU, *B. breve* (A055) 0.1B CFU. She reported that the combination of Vitamin D3 and probiotics improved her symptoms of GERD. A score of 3 was reported.

Subject F was a 15 year-old Caucasian male with allergic rhinitis and nasal polyposis who had been on subcutaneous immunotherapy for 2 years. He reported supplementing daily for 30 days with Vitamin D3 2000 IU and 2 capsules of the probiotic AOR-3. AOR-3 was reported to comprise *E. faecium* T-110 36M CFU, *C. butyricum* TO-A 1.2 M CFU, and *B. subtilis* TO-A 1.2 M CFU. He reported that since starting the combination of the probiotic and Vitamin D3 he noticed some benefit, with decreased symptoms of allergic rhinitis and congestion. A score of 3 was reported.

Subject G was a 20 month old Caucasian female with IgE mediated food allergy to peanut, walnut, and egg, atopic dermatitis, allergic rhinitis. Subject G had undergone oral food challenge and reaction to peanut, egg and walnut. She had undergone oral desensitization to walnut, peanut and egg after tolerating small doses during challenge procedure. Her parents reported supplementation daily for 7 months with Vitamin D3 1000 IU and *L. Rhamnosus* 10B CFU. Subject G's parents reported that Subject G had less severe atopic dermatitis, and tolerated escalating doses of egg, peanut and walnut, as well as decreased severity of allergic rhinitis since starting these supplements 7 months prior. Subject G's parents reported marked improvement since beginning supplementation. A score of 4 was reported.

Subject H was a 42 year-old Caucasian female with a history of recurrent pneumonia, recurrent acute sinusitis, asthma, and a history of poor response to polysaccharide pneumococcal vaccine (PPSV23). Subject H reported supplemented daily for 80 days with Vitamin D3 5000 IU and AOR-3. AOR-3 was reported to comprise *E. faecium* T-110 36M CFU, *C. butyricum* TO-A 1.2 M CFU, and *B. subtilis* TO-A 1.2 M CFU. She demonstrated a significantly improved response to revaccination with PPSV23 vaccine and had a significant reduction in recurrent pneumonia in the 2.5 months since beginning supplementation with a self reported marked improvement since starting. A score of 4 was reported.

Subject I was a 4 year-old Caucasian male with food allergy and atopic dermatitis whose parents report supplementing daily for 45 days with Vitamin D3 1000 IU and *L. rhamnosus* 5B CFU. Subject I's parents reported improvement in Subject I's atopic dermatitis since beginning supplementation, felt the supplements have been of some benefit, and reported a score of 3.

Subject J was a 6 year-old Caucasian male with allergic rhinitis and atopic dermatitis whose parents report supplementing daily for 47 days with Vitamin D3 1000 IU and *L. rhamnosus* 10B CFU. Subject J noticed some improvement in his skin and rhinitis symptoms since beginning to supplement, and reported a score of 3.

Subject K was a 7 year-old Caucasian male with atopic dermatitis and allergic rhinitis who supplemented daily for 50 days with Vitamin D3 1000 IU and two tablets of Bio-three. Bio-three was reported to comprise *E. faecium* T-110 36 M CFU, *C. butyricum* TO-A 1.2 M CFU, and *B. subtilis* TO-A 1.2 M CFU. He reported some improvement in symptoms since beginning to supplement in addition to his routine medications which included a topical intranasal steroid and daily antihistamine. Subject K reported a score of 3.

Subject L was a 35 year-old Caucasian female with chronic sinusitis and allergic rhinitis who supplemented daily for 46 days with Vitamin D3 2000 IU and 2 capsules of AOR-3. AOR-3 was reported to comprise *E. faecium* T-110 36M CFU, *C. butyricum* TO-A 1.2 M CFU, and *B. subtilis* TO-A 1.2 M CFU. Subject L reported that she had decreased allergy and sinus symptoms, as well as no sinus infections, which had been monthly, since initiating supplement. Subject L could not identify if improvement were related to change in season, medications or supplement, but felt at least some benefit related to supplement. A score of 3 was reported.

Subject M was a 42 year-old Caucasian female with a history of chronic sinusitis, allergic rhinitis, and anosmia who initiated subcutaneous immunotherapy (SCIT) 9 months ago. She had previously discontinued specific SCIT 3 years ago due to severe large local reactions to SCIT and a systemic anaphylaxis associated with it. She reported supplementing daily for 42 days with Vitamin D3 2000 IU and 2 tablets of Bio-three. Bio-three was reported to comprise *E. faecium* T-110 36 M CFU, *C. butyricum* TO-A 1.2 M CFU, and *B. subtilis* TO-A 1.2 M CFU. She reported some benefit from supplements as the size of her SCIT reactions has decreased. She reported not having the severe fatigue associated with SCIT since initiating therapy. A score of 3 was reported.

What is claimed is:

1. A composition comprising a first amount of a Vitamin D compound and a second amount of a probiotic compound, wherein the probiotic compound comprises *Clostridium butyricum*.

2. The composition of claim 1, wherein the Vitamin D compound comprises a Vitamin D3 compound.

3. The composition of claim 1, wherein the first amount of the Vitamin D compound comprises about 1000 IU, about 2000 IU, or about 4000 IU of the Vitamin D compound.

4. The composition of claim 1, wherein the second amount of the probiotic compound comprises about 3M CFU, about 10M CFU, about 1B CFU, or about 10B CFU of the probiotic compound.

* * * * *